United States Patent [19]

Goedemans

[11] 4,348,375
[45] Sep. 7, 1982

[54] RADIOASSAY PROCESS AND COMPOSITIONS USEFUL THEREIN

[75] Inventor: Wilhelmus T. Goedemans, Schoorl, Netherlands

[73] Assignee: Byk-Mallinckrodt CIL B.V., Netherlands

[21] Appl. No.: 108,575

[22] Filed: Dec. 31, 1979

[51] Int. Cl.$^3$ .................... A61K 49/00; A61K 43/00
[52] U.S. Cl. ............................................ 424/1; 424/9
[58] Field of Search ......................................... 424/1, 9

[56] References Cited
U.S. PATENT DOCUMENTS
4,017,596  4/1977  Loberg et al. ........................... 424/1

OTHER PUBLICATIONS

Heindel et al., Ed., The Chemistry of Radiopharmaceuticals, Masson Publishing, U.S.A, Inc., New York, 1978, p. 43.

Merrick et al., from Medical Radioisotope Scintigraphy, 1972, IAEA, Vienna, 1973.

Primary Examiner—Christine M. Nucker
Attorney, Agent, or Firm—Bernard, Rothwell & Brown

[57] ABSTRACT

There are disclosed aqueous, radioassaying solutions of a chelate of radioactive indium and an 8-hydroxyquinoline, having an essential absence of an organic solvent, e.g., alcohol or chloroform. The solutions are useful in radioassaying warmblooded animals.

13 Claims, No Drawings

RADIOASSAY PROCESS AND COMPOSITIONS USEFUL THEREIN

The present invention relates to solutions that are useful in radioassaying warmblooded animals and to such procedures using the solutions.

It is highly desirable to radioassay the bodies of warmblooded animals to make various determinations. The use of radioactive indium complexes with 8-hydroxyquinoline for these purposes is known. In "INDIUM-111 LABELED PLATELETS: STUDIES ON PREPARATION AND EVALUATION OF IN VITRO AND IN VIVO FUNCTIONS", Mathew L. Thakur et al., THROMBOSIS RESEARCH, Vol. 9, 345–347, 1976, blood platelets were labeled in vitro with a lipid-soluble complex of indium-111 and 8-hydroxyquinoline (indium-111 oxinate), and injected into warmblooded animals. External radio imaging was then used to locate venous thrombi and damaged areas of arteries. Nancy L. Ascher et al. describe in "Indium 111 Autologous Tagged Leukocytes in the Diagnosis of Intraperitoneal Sepsis", Arch. Surg., Vol. 114, 386–392, April, 1979, the injection of indium-111 oxinate-labeled, autologous, polymorphonuclear leukocytes in warmblooded animals as a means of locating by external radio scanning the location of infections or inflammations. The location of body abscesses has been described in Mathew L. Thakur et al. in "Indium-111-Labeled Autologous Leukocytes in Man", Journal of Nuclear Medicine, Vol. 18, No. 10, 1014–1021, and the procedure involved the external labeling of isolated autologous leukocytes for injection into the body and subsequent examination by external imaging.

Chelates of radioactive indium-111 or indium-113m and 8-hydroxyquinoline are among the complexes disclosed in U.S. Pat. No. 4,017,596, as being useful in radiopharmaceutical external imaging. The direct injection of technetium, gallium and cobalt radioactive agents into mice and dogs is described. The agents are said to have a high degree of in vivo stability, being highly specific to accumulation in certain organs or anatomical areas, and exhibiting excellent nuclear imaging properties.

In copending patent application Ser. No. 105,202, filed Dec. 19, 1979, there is described the in vivo use of radioactive indium oxinates to determine in warmblooded animals the location of inflamed areas. The inflammation may have various causes such as body abscesses, infections, organ transplants employing real or artifical organs, bone prothesis, the presence of other alien object in the body, or other injury. Such procedures avoid the highly undesirable invasion of the body as by surgery or introduction of a mechanical device into the body in the area of inflammation which can be painful and may require the exercise of a great deal of skill. Also, a method involving the direct injection of the radioactive agent into the body is relatively rapid and convenient, and avoids the use of external or in vitro tagging procedures.

In these and other prior studies the radioactive indium oxinate has been utilized as a solution containing an organic solvent such as an alcohol, usually ethanol. The solutions generally have the disadvantage of containing sufficient amounts of the solvent for the solutions to be hypertonic. It is known that a 1.39% solution of ethanol in water is isotonic. This means that the concentrations of ethanol as reported in the literature, i.e., 25%, are many times hypertonic. Addition of salt to these solutions does still increase the tonics. Also, chloroform solvents have been employed, especially in preparing the solution that is used to radiotag blood components. Organic solvents generally have other undesirable properties for administration to the bodies of warmblooded animals and may exhibit toxic effects, even when used in very small amounts, and the avoidance of these materials is radioactive assaying solutions destined for such use is quite desirable.

In spite of these disadvantages, solutions of radioactive indium oxinates employed in radioassay procedures have contained ethanol in such amounts that the solutions are hypertonic, see, for example, the above-cited Thakur et al. publications. The Thrombosis Research article discloses on pages 346 and 347, indium-111 oxine in saline, hypertonic solutions containing the oxine and ethanol. Similar solutions are described in "Survey of Radioactive Agents for In Vitro Labeling of Phagocytic Leukocytes, I. Soluble Agents", McAfee et al., Journal of Nuclear Medicine, Vol. 17, No. 6, pp. 480–487, 1976; "The Radiolabeling of Lymphocytes and Tumor Cells with 111 Indium (39991)", Frost et al., Proceedings of the Society for Experimental Biology and Medicine, Vol. 157, pp. 61–65, 1978; and Ascher et al., supra. In U.S. Pat. No. 4,017,596 there has not been found any description of an indium oxinate solution. From these articles it is apparent that organic solvent-containing solutions were considered to be necessary for accomplishing the desired survey, apparently this was done as a means of obtaining adequate dissolution of the lipid-soluble chelate in the aqueous solution and the desired effectiveness when using the solution.

By the present invention the use of organic solvent components is avoided, as are problems that may arise by the presence of an organic solvent component in solutions containing a radioactive indium oxinate for injection into the body of warmblooded animals. Contrary to prior practices, the radioactive indium oxinate solutions can avoid the use of organic solvents, and the solutions may be used successfully in radioassaying procedures in warmblooded animals whether the blood components be labeled in vivo or in vitro. The present invention provides essentially organic solvent-free, aqueous solutions of radioactive indium oxinates whose use in radioassaying procedures usually provides results that are comparable with, or even better than, those obtained when employing ethanol-containing solutions. Moreover, the absence of organic solvents in the solutions reduces the chances of obtaining toxic effects, and the solutions can generally have the advantage of being essentially isotonic.

The compositions of the present invention can be used in various methods of radioassaying in which blood components are tagged either in vitro or in vivo. The tagged blood components may be red or white cells or platelets. In in vitro procedures the blood component to be tagged is generally isolated from a blood sample and then tagged and placed in the body of a warmblooded animal. In in vivo methods the tagging agent is directly administered to the body and tagging occurs in situ. In such cases, tagging may be less selective among the various blood components present. In either procedure the location of accumulations of radioactivity in the body can be determined by external imaging.

For example, in a process in which a body abscess or other inflammation reaction is located, a radioactive chelate of indium and an 8-hydroxyquinoline is placed in the bloodstream of the animal. After a suitable period, the chelate accumulates not only in certain areas of the body such as the liver and spleen, but, also, in relatively large amounts in any inflamed area present due to various causes such as those described above. The body can then be subjected to a radio survey by an external imaging technique to detect the accumulated radioactivity in the location of the inflamed area providing the latter is in a part of the body other than one in which the chelate would normally accumulate to essentially the same extent even in the absence of an abscess. This procedure is relatively rapid and convenient, and avoids the use of external or in vitro tagging procedures which, however, can be employed for similar purposes using the compositions of the present invention.

The present invention is based on the finding that aqueous, essentially organic solvent-free solutions of radioactive indium chelates of an 8-hydroxyquinoline can be provided in small, effective amounts in warm-blooded animals for the purpose of accomplishing a radiosurvey of the body by external imaging. Alternatively, the radioactive chelates can be used to tag blood components in vitro, and the radioactive materials administered in small effective amounts to such bodies for similar purposes. The various types of radioassays discussed above can be performed by using the compositions of the invention.

Various mammals can be treated by these procedures including, for example, dogs, goats, humans, rodents, and the like. The indium chelates of an 8-hydroxyquinoline can be the indium-111 or indium-113m complexes described in U.S. Pat. No. 4,017,596, and thus, may be 8-hydroxyquinoline in unsubstituted or substituted forms which have substantially equivalent complex constants and hydrophilic properties. In the latter case, the substituted moiety may be, for instance, one or more hydrocarbyl groups, for example, alkyl such as methyl or other lower alkyl groups, or other substituents. Of course, the chelate should not unduly adversely affect the body in which the agent is provided.

The compositions of the present invention are aqueous solutions containing a radioactive chelate of indium and an 8-hydroxyquinoline in solution, but having an essentially complete absence of an organic solvent component, e.g., alcohol, such as ethanol. The organic solvent-free, aqueous solutions of the invention contain water as the major component with the indium chelate being present in small, effective amounts suitable for use in radioassaying. The solutions may contain a minor amount of salt, e.g., sodium chloride, or other inorganic salts may be present in small amounts in the presence or absence of sodium chloride. The salts can be used in amounts sufficient to provide an essentially isotonic solution, and this amount may depend on any other ingredients that are present, e.g., buffers. If present, the quantity of sodium chloride in the solution may, for example, be at least about 0.1 up to about 1 weight percent, preferably up to 0.5 weight percent, although larger amounts, say up to about 0.7 weight percent or even up to about 0.9 weight percent or so, may be present.

The pH of the solutions of the invention has been found to be relatively unimportant. For in vitro labelling a pH of about 6 to 7 could be optimal; however, a pH of less than about 4.2 for a solution to be marketed may be advantageous to decrease the adsorption of indium-111 activity on glass equipment it contacts. Also, the solutions may contain buffers or other ingredients as desired. For distribution, we prefer to prepare solutions having a pH of about 3 and the user of the solution may bring the pH up to the approximate 6 to 7 range before use. If a relatively small amount of sodium chloride be present, additional buffer, e.g., sodium acetate may be needed to bring the solution to isotonicity. This in turn may require the user to employ a larger amount of buffer, e.g., a sodium phosphate, to reach the optimal pH for cell labelling.

In the methods of the present invention the indium chelate, or blood components tagged in vitro by use of the chelate can be administered to the animal as by intravenous or subcutaneous administration, and the amount of imaging agent introduced may be quite small. Generally, the chelate can be introduced into the body in an amount up to about 0.036 millicurie of radioactivity per pound of body weight, and, preferably, this amount need not exceed about 0.0143 millicurie per pound. The amount should be sufficient so that the agent accumulated in a given area of the body can be effectively detected, for example, at least about 0.00036 millicurie, preferably at least about 0.0036 millicurie, per pound of body weight. The radioactive agent may be applied as an aqueous solution containing a small effective amount of the chelate as oxine, for instance, about 0.005 to 0.2 milligram, preferably about 0.01 to 0.5 milligram, per milliliter of solution. The amount of solution administered need not exceed more than a few milliliters, preferably being less than about 5, and the amount need only be sufficient to enable the desired detection to be subsequently made, e.g., at least about 0.0036 milliliter per pound of body weight. Frequently, these amounts are about 0.007 to 0.014 milliliter of solution per pound of body weight. The solution may often have above 0.02 to 5 or 10 millicuries of radioactivity per milliliter of solution, preferably about 0.1 to 0.5 millicurie per milliliter.

After the radioactive imaging agent has been introduced into the body of the animal, the radioassay may be accomplished by utilizing various radioscanning techniques employing gamma ray detection such as by scintillation camera and the like. Generally, it has been found that the desired accumulation of radioactivity may occur sufficiently for detection after about one hour or so and the life of the radioactive indium imaging agent may be sufficiently extended to permit the scanning to be accomplished up to several days after injection into the body. At the same time, however, this life is not so extended that it poses an excessive radiation burden to the body. The accumulated radioactivity may be detected in various areas of the body, e.g., in an organ such as the liver or kidneys, or in an inflamed area, as noted above in connection with prior assaying procedures employing radioactive indium.

The solution of the invention can be used to conduct in vitro or in vivo radioassays of the types described above. In in vitro procedures the radioactive indium material, e.g., indium-111 oxinate, can label cellular blood components such as granulocytes, lymphocytes, platelets, and erythrocytes. These cells may be used to locate, for example, body organs, abscesses and other inflammatory reactions, myocardial infractions, thrombus formation, and rejection of transplanted organs. As known, labelled erythrocytes have been extensively used for measuring blood volume. Indium-111 labelled erythrocytes show cardiac, liver and spleen blood pool activity 24 hours after intravenous administration. The solutions of the invention may be used for these and other purposes.

Cell labelling can be carried out by addition to the solution of a cell preparation which is preferably suspended in buffered saline or any other appropriate physiological medium without plasma proteins. After gently mixing, the composite can be incubated for at least twenty minutes at room temperature to achieve efficient labelling, except in labelling thrombocytes longer incubation times of up to one hour or more may be needed. Labelling efficiency is dependent on the number of cells in the incubation mixture. Depending on the labelling efficiency, washing of the cells is recommended to remove any free indium-111 oxinate. Thereafter the labelled cells can be resuspended in their own plasma medium.

In case of labelling leukocytes and thrombocytes care should be taken that the isolation procedure for the cells is as minimal as possible to avoid damage to the cells. For example, in case of human leukocytes it is sufficient to sediment the erythrocytes (25 ml fresh ACD blood) by gravitational force for one hour at room temperature. The plasma supernatant to be removed contains almost all leukocytes which can be labelled with indium-111 oxinate preferably after one washing in buffered saline.

As an example, cell labelling has been accomplished by washing bovine erythrocytes twice with saline and then suspending the cells in saline 1:3 V/V. A useful formulation of the invention may contain in 1 ml, 1 mCi, indium-111 chelated with 25 $\mu$g of oxine to which sufficient 0.03 molar acetate buffer is added to give a pH of 3. The solution can be brought to isotonicity by the addition of 5.62 mg sodium chloride. To one vial containing 1 ml (=1 mCi) In-111 oxinate, 0.5 ml of 0.11 M $Na_2HPO_4.2H_2O$ is added to raise the pH to 6.5 (19.58 g/liter). The final solution is isotonic and may be used in either in vitro or in vivo radioassaying procedures.

Labelling of bovine erythrocytes has been carried out by addition to the isotonic solution of 3 ml of a 33% erythrocyte suspension and incubation for 20 minutes at room temperature; labelling efficiency is determined after separation of cells and fluid by centrifugation, by measuring the relative radioactivity of the cells and dividing by the initial radioactivity. The labelling efficiency is 96%. The labelled cells are then incubated in bovine plasma for another half hour at room temperature. Cells and plasma are separated by centrifugation and only 2% of the radioactivity appears in the plasma. The cells can be used to conduct a radioassay of warmblooded animals, e.g., humans, according to known procedures.

In the radioassaying process of the invention, the in vitro-labeled, bovine granulocyte can be used as an aid to the diagnosis and localization of bacterial body abscesses. Indium-111 is a suitable isotope for scanning and gamma camera imaging, with a half-life (68 hours) which is long enough to enable scanning to be continued for up to about 3 to 4 days, yet not so long it poses an excessive radiation burden. Indium will not itself label cells, but will when chelated to a lipophilic 8-hydroxyquinoline (oxine) molecule which transports it through the cell membrane and into the cell. The cell is then firmly labeled as the indium is unable to return through the cell membrane.

The viable, labeled granulocyte suspension can be administered intravenously to a goat containing a bacterial abscess. For scintigraphy the goats can be sedated with 1.5 ml Vetranquil (Philips-Duphar B.V., Amsterdam, Holland) and kept in the proper position under the gamma ray camera after injection of the In-111-oxinate labeled autologous cells.

After the injection the goat is imaged by scintigraphy the next day. The tissue distribution of In-111 in the goat is determined to show the distribution of radioactivity among the organs. To confirm the results the goat is sacrificed and high radioactivity is found in the kidney. An inflamed lymph node has three times the radioactivity of a non-inflamed one. The abscess has a moderate radioactivity accumulation, more than blood and muscles; however, far less than, for example, the ovaria, uterus, lungs, kidneys and spleen. So only with the low local background of the flank of the abdomen is it possible to visualize the abscess. This result may, however, be due to the choice of animal. Heart muscle shows moderate accumulation of radioactivity compared to blood. The determinations on the dissected animal parts are in agreement with those made by external scanning of the body.

The clearance of In-111 from the blood of the goat can be followed after an intravenous injection in order to determine the biological half life for the formulation. After injection, 10 ml blood samples are taken at intervals. All blood samples are subjected to differential centrifugation in order to determine whether the radioactivity is localized in the plasma, platelets, red cell fraction or leukocytes. Platelet rich plasma (PRP) is prepared by centrifugation of heparinised blood at 200 g during 15 minutes. After sampling of the PRP (1 ml) the residue is centrifuged at 1600 g for 10 minutes. 1 ml samples are taken from the plasma layer (platelet poor plasma=PPP), from the interface between plasma and red cells (leukocytes) and from the red cell fraction. The radioactivities are determined and clearance is determined corrected for physical decay.

To illustrate the in vivo labelling process of the invention a goat with a bacterial abscess 2 months old is injected with the In-111 oxinate (ca. 1 mCi) solution of the invention described above. The goat is imaged by gamma camera the next day. The abscess shows up as a clear spot on the photograph. The goat is sacrificed and the distribution of radioactivity between the different tissues and organs determined. There is a strong accumulation of In-111 in the cell fraction of the blood, almost as much as the radioactivity per gram of tissue of the spleen. An additional washing of the cells with PBS showed that the radioactivity is firmly bound. Tissue of the abscess has a high accumulation of In-111, similar to the kidney and ovarium. This is in correspondence with the clear spot on the gamma camera pictures. Pus of the abscess contained little radioactivity. The fat, muscle, marrow from the femur, gall, faeces, pancreas and urine show no significant accumulation of radioactivity. Heart muscle shows a moderate accumulation of In-111.

I claim:

1. A method for radioassaying a warmblooded animal which comprises administering to said animal an essentially organic solvent-free, aqueous solution containing a small amount of a radioactive indium-8-hydroxyquinoline or blood cells radioactivity labeled by said solution, said amount being sufficient for detection by external imaging, and subjecting said animal to external imaging for detecting accumulated radioactivity to determine its location in the body of said animal.

2. A method of claim 1 in which said animal is a mammal.

3. A method of claim 1 or 2 in which said animal has an inflamed area, the location of which is thereby detected.

4. A method of claim 1 or 2 in which the radioactive material is indium-111-8-hydroxyquinoline.

5. A method of claim 4 in which said animal has an inflamed area, the location of which is thereby detected.

6. A method of claim 1 or 2 in which the radioactive material administered to said animal contains about 0.02 to 10 millicuries of radioactivity per milliliter.

7. A method of claim 6 in which said animal has an inflamed area, the location of which is thereby detected.

8. An aqueous solution containing a small amount of a radioactive indium-8-hydroxyquinoline suitable for use in radioassaying and being essentially free of organic solvent.

9. A solution of claim 8 in which the radioactive material is indium-111-8-hydroxyquinoline.

10. A solution of claim 8 or 9 in which the amount of indium-8-hydroxyquinoline as an oxine is about 0.005 to 0.2 milligram per milliliter.

11. A solution of claim 8 or 9 which contains a small amount of sodium chloride sufficient for the solution to be isotonic.

12. A solution of claim 11 in which the amount of sodium chloride is about 0.1 to 1 weight percent.

13. A solution of claim 12 in which the amount of indium-8-hydroxyquinoline as an oxine is about 0.005 to 0.2 milligram per milliliter.

* * * * *

UNITED STATES PATENT AND TRADEMARK OFFICE
CERTIFICATE OF CORRECTION

PATENT NO. : 4,348,375
DATED : September 7, 1982
INVENTOR(S) : Goedemans

It is certified that error appears in the above-identified patent and that said Letters Patent is hereby corrected as shown below:

Column 1, line 29, "in" should be "by".

Column 2, line 9, "is" should be "in".

Column 5, line 59, "not so long it" should be "not so long that it".

Column 6, claim 1, line 62, "radioactivity" should be "radioactively".

Signed and Sealed this

Twenty-second Day of February 1983

[SEAL]

Attest:

GERALD J. MOSSINGHOFF

*Attesting Officer*    *Commissioner of Patents and Trademarks*